United States Patent [19]
Noda et al.

[11] Patent Number: 5,780,368
[45] Date of Patent: Jul. 14, 1998

[54] SPRAY PROCESSES USING A GASEOUS FLOW FOR PREPARING BIODEGRADABLE FIBRILS, NONWOVEN FABRICS COMPRISING BIODEGRADABLE FIBRILS, AND ARTICLES COMPRISING SUCH NONWOVEN FABRICS

[76] Inventors: Isao Noda; Reinhold August Lampe; Michael Matthew Satkowski, all of The Procter & Gamble Company, Miami Valley Laboratories, P.O. Box 398707, Cincinnati, Ohio 45239-8707

[21] Appl. No.: 203,260

[22] Filed: Feb. 28, 1994

Related U.S. Application Data

[63] Continuation-in-part of Ser. No. 187,969, Jan. 28, 1994, abandoned, Ser. No. 188,271, Jan. 28, 1994, abandoned, and Ser. No. 189,029, Jan. 28, 1994, abandoned.

[51] Int. Cl.$^6$ .................................................. B32B 27/00
[52] U.S. Cl. .................. 442/334; 442/335; 442/392
[58] Field of Search ........................... 428/288, 903; 442/392, 334, 335

[56] References Cited

U.S. PATENT DOCUMENTS

| | | | |
|---|---|---|---|
| 2,988,782 | 6/1961 | Parrish et al. | 18/48 |
| 2,999,788 | 9/1961 | Morgan | 162/146 |
| 3,743,272 | 7/1973 | Nowotny et al. | 264/69 |
| 3,831,317 | 8/1974 | Porte | 47/58 |
| 3,849,040 | 11/1974 | McGinnis et al. | 425/72 |
| 3,882,095 | 5/1975 | Fowells et al. | 260/88.2 R |
| 4,013,751 | 3/1977 | Davis et al. | 264/140 |
| 4,047,862 | 9/1977 | Keith | 425/8 |
| 4,091,058 | 5/1978 | Sander et al. | 264/11 |
| 4,098,640 | 7/1978 | Sander et al. | 162/146 |
| 4,187,143 | 2/1980 | Sander et al. | 162/157 |
| 4,196,305 | 4/1980 | Murphy et al. | 568/758 |
| 4,219,512 | 8/1980 | Sinn et al. | 264/11 |
| 4,224,259 | 9/1980 | Sander et al. | 264/11 |
| 4,374,788 | 2/1983 | Gonzales | 264/5 |
| 4,603,070 | 7/1986 | Steel et al. | 428/88 |
| 4,642,262 | 2/1987 | Piotrowski et al. | 428/296 |
| 4,915,893 | 4/1990 | Gogolewski et al. | 264/205 |
| 4,944,734 | 7/1990 | Wallach | 604/358 |
| 5,026,589 | 6/1991 | Schechtman | 428/138 |
| 5,053,482 | 10/1991 | Tietz | 528/272 |
| 5,110,852 | 5/1992 | Gogolewski et al. | 524/108 |
| 5,114,537 | 5/1992 | Scott et al. | 162/146 |
| 5,300,358 | 4/1994 | Evers | 428/913 |
| 5,336,551 | 8/1994 | Graiver et al. | 428/220 |

FOREIGN PATENT DOCUMENTS

| | | |
|---|---|---|
| 897923 | 4/1972 | Canada . |
| 0 176 316 | 4/1986 | European Pat. Off. . |
| 0 177 207 | 4/1986 | European Pat. Off. . |
| 0 272 902 | 6/1988 | European Pat. Off. . |
| 0 534 562 A1 | 3/1993 | European Pat. Off. . |
| 4016-348-A | 11/1991 | Germany . |
| 41 19 455 | 9/1992 | Germany . |
| 54-120-727 | 9/1979 | Japan . |
| 0 4036-320-A | 2/1992 | Japan . |
| 5 9088-915-A | 5/1994 | Japan . |
| 2 243 327 | 10/1991 | United Kingdom . |
| 94/00506 | 1/1994 | WIPO . |
| 94/08078 | 4/1994 | WIPO . |

OTHER PUBLICATIONS

Drelich, A., "Thermal Bonding With Fusible Fibers", Nonwovens Industry, pp. 12–26 (Sep. 1985).
Gordon, W., H.J. Leugering and H. Cherfron, "Polyethylene Fibrids: Preparation and Properties" Angew. Chem. Int. Ed. Engl. vol. 17, pp. 820–825 (1978).
Rave, T.W., "Synthetic Pulp", Chemtech, pp. 54–62 (Jan. 1985).
BIOPOL Processing Fibres, Product description, Marlborough Biopolymers Ltd.

*Primary Examiner*—James J. Bell
*Attorney, Agent, or Firm*—Carl J. Roof; Bart S. Hersko; David L. Suter

[57] ABSTRACT

The present invention comprises processes for preparing biodegradable fibrils from one or more biodegradable homopolymeric or copolymeric resins, said process comprising: a) forming a liquid resin mixture by melting or solvating the resin or resins; and b) introducing the liquid resin mixture to a flow of a gaseous substance. The present invention further comprises biodegradable fibrils made according to the processes of the present invention. The invention further comprises nonwoven fabrics comprising biodegradable fibrils. The invention further comprises disposable absorbent articles comprising a water-permeable topsheet, an absorbent core, and a water-impermeable backsheet, wherein the topsheet comprises a nonwoven substrate comprising biodegradable fibrils. The invention further comprises disposable articles comprising biodegradable fibrils.

16 Claims, No Drawings

SPRAY PROCESSES USING A GASEOUS FLOW FOR PREPARING BIODEGRADABLE FIBRILS, NONWOVEN FABRICS COMPRISING BIODEGRADABLE FIBRILS, AND ARTICLES COMPRISING SUCH NONWOVEN FABRICS

This is a continuation-in-part of Ser. No. 08/187,969 filed Jan. 28, 1994 now abandoned; Ser. No. 08/188,271 filed Jan. 28, 1994 now abandoned; Ser. No. 08/189,029 filed Jan. 28, 1994 now abandoned.

TECHNICAL FIELD

The present invention relates to the processing of biodegradable polymers and products comprised of biodegradable polymers. In particular, the present invention relates to the processing of biodegradable polymers into fibrils, which can be further processed into nonwovens.

BACKGROUND OF THE INVENTION

Polymers find uses in a variety of plastic articles including films, sheets, fibers, foams, molded articles, adhesives and many other specialty products. The majority of this plastic material ends up in the solid waste stream, headed for rapidly vanishing and increasingly expensive landfill space. While some efforts at recycling have been made, the nature of polymers and the way they are produced and converted to products limits the number of possible recycling applications. Repeated processing of even pure polymers results in degradation of material and consequently poor mechanical properties. Different grades of chemically similar plastics (e.g., polyethylenes of different molecular weights, as used in milk jugs and grocery sacks) mixed upon collection can cause processing problems that make the reclaimed material inferior or unusable.

Absorbent article applications such as diapers, sanitary napkins, pantiliners and the like, involve several different types of plastics. In these cases, recycling is particularly costly because of the difficulty in separating the different components. Disposable products of this type generally comprise some sort of fluid-pervious topsheet material, an absorbent core, and a fluid-impervious backsheet material. Such absorbent structures are typically prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

A conventional disposable absorbent product is already to a large extent compostable. A typical disposable diaper, for example, consists of about 80% of compostable materials, e.g., wood pulp fibers, and the like. In the composting process soiled disposable absorbent articles are shredded and commingled with organic waste prior to the composting per se. After composting is complete, the non-compostable particles are screened out. In this manner even today's absorbent articles can successfully be processed in commercial composting plants.

Nevertheless, there is a need for reducing the amount of non-compostable materials in disposable absorbent articles. There is a particular need to replace polyethylene and polypropylene topsheets in absorbent articles with liquid pervious compostable material.

In addition to being compostable, materials used for topsheets must satisfy many other performance requirements for satisfying the end user's needs. For example, these materials must be capable of being processed to provide substrates that are comfortable to touch. In addition, topsheets must possess sufficient properties such as impact strength, moisture transmission, etc.

Certain biodegradable resins are well known, but often do not have good fiber or film forming properties. Polymer resins comprising poly(hydroxybutyrate) (PHB) are particularly ill-suited for fiber and film formation. These resins are typically of slow crystallization rates, have low melt viscosity, degrade near their melt temperatures and are rigid when solidified. Accordingly, such resins often cannot be processed by conventional means of film or filament formation. Indeed, when formed into films, biodegradable resins comprising PHB are generally not flexible. The inflexibility of such films hinders their use in absorbent articles, particularly when used as topsheets, as these materials are in direct contact with the skin of the wearer.

For the foregoing reasons, there is a continuing need for biodegradable materials that can be used in absorbent articles. In particular, there is a need for a biodegradable substrate which is flexible and durable, but also provides a comfortable texture when used in, for example, absorbent articles.

It is an object of the present invention to provide biodegradable fibrils that can be processed to give flexible, nonwoven fabrics which are soft and clothlike to the touch. A further object of the invention is to provide a process for making such biodegradable fibrils. Another object is to provide a biodegradable nonwoven fabric comprising biodegradable fibrils. Still another object is to provide disposable absorbent articles comprising such biodegradable fabrics. Still another object is to provide textiles comprising biodegradable fibrils.

SUMMARY OF THE INVENTION

The present invention encompasses a process for making biodegradable fibrils from one or more biodegradable resins. The processes are particularly useful in forming fibrils from resins comprising PHB, but can also be utilized with other biodegradable resins. The resins used in the process can be biodegradable homopolymers, copolymers or mixtures thereof. The process comprises forming a liquid resin mixture comprising one or more biodegradable resins by melting or solvating the biodegradable resin(s), followed by introduction of the liquid resin mixture to a flow of a gaseous substance. The resulting fibrils are collected on a suitable collecting device, and are then processed according to their desired end use.

The invention further comprises biodegradable fibrils prepared according to the processes of the present invention.

The invention further encompasses a nonwoven fabric comprising biodegradable fibrils. These fabrics are useful in articles such as diapers, incontinence articles, sanitary napkins, and the like. Preferred fabrics comprise biodegradable fibrils prepared by the process of the present invention.

The invention further encompasses disposable absorbent articles comprising a water-permeable topsheet, an absorbent core, and a water-impermeable backsheet, wherein the topsheet comprises a nonwoven substrate comprising biodegradable fibrils. Other absorbent articles according to this invention are those wherein the backsheet is also comprised of biodegradable fibrils. Preferred are those articles wherein the biodegradable nonwoven component is comprised of fibrils made according to the processes of the present invention.

Any desirable absorbent core can be utilized with the biodegradable fabrics of the present invention to provide absorbent articles within the scope of the present invention. Preferred materials useful as the absorbent core include wood pulp fibers or wood pulp fibers in combination with absorbent gelling materials.

The invention further encompasses textiles comprising the biodegradable fibrils of the present invention.

DETAILED DESCRIPTION

Definitions

The following is a list of definitions for terms used herein.

"Alkenyl" means a carbon-containing chain which may be monounsaturated (i.e., one double bond in the chain) or polyunsaturated (i.e., two or more double bonds in the chain); straight or branched; and substituted (mono- or poly-) or unsubstituted.

"Alkyl" means a saturated carbon-containing chain which may be straight or branched; and substituted (mono- or poly-) or unsubstituted.

"Biodegradable" means a material capable of being broken down into small chemical subunits which can be utilized in the food chain through naturally acting and/or environmentally safe enzymes, bacteria, spores and the like. Preferably, the material is capable of being broken down into water and $CO_2$.

A "biodegradable polymer" is any polymer that is biodegradable, as that term is defined herein.

"Compostable" means a material that meets the following three requirements: (1) the material is capable of being processed in a composting facility for solid waste; (2) if so processed, the material will end up in the final compost; and (3) if the compost is used in the soil, the material will ultimately biodegrade in the soil.

The requirement that the material ends up in the final compost typically means that it undergoes a form of degradation in the composting process. Typically, the solid waste stream will be subjected to a shredding step in an early phase of the composting process. As a result, materials will be present as shreds rather than a sheet. In the final phase of the composting process, the finished compost will be subjected to a screening step. Typically, the polymer shreds will not pass through the screens if they have retained the size they had immediately after the shredding step. The compostable materials of the present invention will have lost enough of their integrity during the composting process to allow partially degraded shreds to pass through the screens. However, it is conceivable that a composting facility might subject the solid waste stream to a very rigorous shredding and a rather coarse screening, in which case nondegradable polymers like polyethylene would meet requirement (2). Therefore, meeting requirement (2) is not enough for a material to be compostable within the present definition.

What distinguishes the compostable material as defined herein from material like polyethylene is requirement (3), that the material ultimately biodegrade in the soil. This biodegradability requirement is not essential to the composting process or the use of composting soil. Solid waste and the compost resulting therefrom may contain all kinds of nonbiodegradable materials, for example, sand. However, to avoid a build up of man-made materials in the soil, it is required herein that such materials be fully biodegradable. By the same token, it is not at all necessary that this biodegradation be fast. As long as the material itself and intermediate decomposition products are not toxic or otherwise harmful to the soil or crops, it is fully acceptable that their biodegradation takes several months or even years, since this requirement is present only to avoid an accumulation of man-made materials in the soil.

"Copolymer" and "copolymeric" mean a polymer consisting of two or more different monomeric units.

"Fibrils" means short, fine fibers. The term fibril is discussed in detail herein below.

"Homopolymer" and "homopolymeric" mean a polymer consisting of the same repeating monomeric unit.

"Liquid resin mixture" is a liquid comprising one or more biodegradable resins. The term includes a liquid consisting of one biodegradable resin (e.g., PHB).

"Solvating" means forming an aggregate that comprises a solute ion or molecule with one or more solvent molecules, so as to form a single phase mixture.

Biodegradable Resins

Biodegradable fibrils of the present invention comprise one or more biodegradable polymers or copolymers. The biodegradable resins useful in the present invention can be any resin which is capable of biodegradation. Resins useful herein may be either biologically or synthetically produced. Furthermore, the resins may be either homopolymeric or copolymeric. As used herein, the terms "resin" and "polymer" include both homopolymeric and copolymeric biodegradable polymers. Furthermore, although stated in the singular, these terms include a plurality of "resins" and "polymers".

Biologically produced biodegradable resins include aliphatic polyesters. Specific examples include poly(3-hydroxybutyrate) (PHB), a polymer consisting of the monomeric unit having a structure according to Formula I

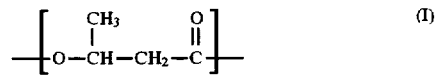

and poly(3-hydroxybutyrate-co-3-hydroxyvalerate) (PHBV), a copolymer which has two randomly repeating monomer units (RRMU) wherein the first RRMU has a structure according to Formula (I) and the second RRMU has a structure according Formula (II)

Such polyesters, and methods for their preparation, are described in U.S. Pat. No. 4,393,167, Holmes et al. issued Jul. 12, 1993 and U.S. Pat. No. 4,880,592, Martini et al., issued Nov. 14, 1989, both of which are incorporated by reference herein. Because of their poor film-forming properties, the processes of the present invention are particularly useful for forming nonwoven fabrics from these resins. Copolymers of PHBV are commercially available from Imperial Chemical Industries under the tradename BIOPOL. An overview of BIOPOL technology is provided in BUSINESS 2000+(Winter, 1990).

U.S. patent application Ser. No. 08/187,969 titled BIODEGRADABLE COPOLYMERS AND PLASTIC ARTICLES COMPRISING BIODEGRADABLE COPOLYMERS, by Noda, filed Jan. 28, 1994, which discloses novel biodegradable copolymers, and methods for making the copolymers, that are also useful in the present invention, is incorporated herein by reference. Briefly, that application describes biodegradable polyhydroxyalkanoate (PHA) copolymers comprising at least two RRMUs wherein the first RRMU has the structure

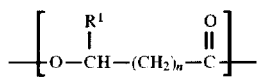

wherein $R^1$ is H, or $C_1$ or $C_2$ alkyl, and n is 1 or 2; the second RRMU has the structure

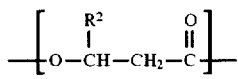

wherein $R^2$ is a $C_4$–$C_{19}$ alkyl or alkenyl; and wherein at least 50% of the RRMUs have the structure of the first RRMU.

U.S. Ser. No. 08/189,029, by Noda, filed Jan. 28, 1994, which discloses novel biodegradable copolymers, and methods for making the copolymers, that are also useful in the present invention, is incorporated herein by reference. Briefly, that application describes biodegradable (PHA) copolymers comprising at least two RRMUs wherein the first RRMU has the structure

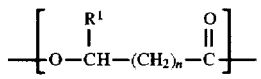

wherein $R^1$ is H or $C_2$ alkyl, and n is 1 or 2; the second RRMU has the structure

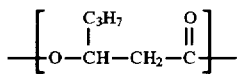

and wherein at least 50% of the RRMUs have the structure of the first RRMU.

U.S. Ser. No. 08/188,271, by Noda, filed Jan. 28, 1994, which discloses biodegradable copolymers that are also useful in the present invention, is incorporated herein by reference. Briefly, that application describes biodegradable copolymers, wherein the copolymers comprise at least two RRMUs wherein the first RRMU monomer unit has the structure

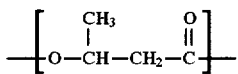

and the second RRMU has the structure

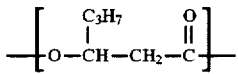

wherein at least 50% of the RRMUs have the structure of the first RRMU.

Other biodegradable resins useful in the present invention include synthetically produced resins. Such synthetically produced resins include aliphatic polyesters, which, along with the methods for making such resins, are known in the art. Examples of such synthetic polyester resins include polylactide (PL), which has a structure according to Formula III; polydioxanone (PDO), which has a structure according to Formula IV; and polycaprolactone (PCL), which has a structure according to Formula V. These resins are described in World Patent Publication No. WO 90/01521, published Feb. 22, 1990 by Sinclair et al.; U.S. Pat. No. 5,026,589, issued Jun. 25, 1991 to Schechtman; and ENCYCLOPEDIA OF POLYMER SCIENCE AND ENGINEERING, Second Edition, Vol. 2, pp 220–243 (1983); all of which are incorporated by reference herein.

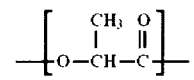 (III)

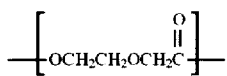 (IV)

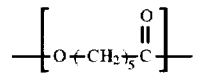 (V)

Still other resins useful in the present invention are polyvinyl alcohols and their copolymers. A preferred polyvinyl alcohol copolymer is the copolymer of ethylene and vinyl alcohol, which has two RRMU wherein the first RRMU has the structure

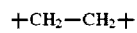

and the second RRMU has the structure

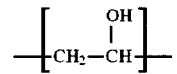

Still other biodegradable resins useful in the present invention are polyethers, such as polyethyleneoxide (PEO) (also referred to polyethyleneglycol), which is also well known in the art.

Another biodegradable resin useful in the present invention is cellulose and its derivatives. An example is cellulose acetate. Cellulose resins, and methods for making them, are well known in the art. See, e.g., ENCYCLOPEDIA OF POLYMER SCIENCE AND ENGINEERING, Second Edition, Vol. 3, pp 181–208 (1983).

The biodegradable resins, including those described specifically above, may be used together to make a polymer blend, where said blend is then used to prepare biodegradable fibrils. Furthermore, as indicated, one or more of the resins used to form the polymer blend may be a copolymer. Such blends include, for example: the combination of two polymers selected from the same type of polymer (for example, two biologically produced polyesters) and the combination of polymers selected from two or more different types of polymers (for example, a biologically produced polyester and a polyvinyl alcohol). While not exhaustive, the following are preferred combinations of polymers useful in preparing the biodegradable fibrils of the present invention: PCL and PHB; PCL and PHBV; PHBV and PHB; PHBV and PEO; and PHB and PEO.

Processes of the Present Invention

The processes of the present invention are useful for forming biodegradable fibrils. The processes are particularly useful for making fibrils from hard-to-process resins, such as biologically produced polyesters, especially PHB polymer and copolymeric resins comprising hydroxybutyrate comonomer units. Nonetheless, the processes are also useful for making fibrils that do not comprise PHB polymer or copolymers comprising hydroxybutyrate comonomer units.

The processes of the present invention use a flow of a gaseous substance to prepare biodegradable fibrils. In particular, the process involves preparing biodegradable fibrils from one or more biodegradable homopolymeric or copolymeric resins, the process comprising: a) forming a liquid resin mixture by melting or solvating the biodegradable resin or resins; and b) introducing the liquid resin mixture to a flow of a gaseous substance. Preferred are those processes where the resin mixture is placed in the liquid state by melting.

When step a) of the process involves melting the resins to form a liquid resin mixture, one skilled in the art appreciates that any suitable means for heating can be utilized. The resin(s) should be heated to a temperature sufficient to liquefy the resins, but not to a level where the resins will decompose or their molecular weight will decrease significantly. Accordingly, the temperature used to melt the resins depends on the resins being utilized. Preferably, the temperature should be from about 0° to about 30° C. above the melting point of the resin having the highest melting point. Most preferably, the temperature should be from about 10° to about 20° C. above the melting point of the resin having the highest melting point.

When step a) of the process involves solvating the resin(s) to form a liquid resin mixture, one skilled in the art appreciates that any suitable means for solvation can be used. The appropriate solvent system must be one that allows thorough mixing if a plurality of resins are used, and must in any event not cause decomposition of the resins used. Preferred solvents include, for example, chloroform, methylene chloride, pyridine, trichloroethane, propylene carbonate, and ethylene carbonate. Particularly preferred are chloroform and methylene chloride. The solvents listed are by way of example, and are not intended to limit the scope of the solvents useful in the processes of the present invention.

Regardless of which method of liquefication is employed in step a), any of a variety of additives may be included when forming the liquid resin mixture. Such additives include plasticizers, nucleating agents, binders, fillers, coloring agents and agents that will render the resulting fibrils hydrophobic (for example, where the fibrils will be used to form a topsheet for an absorbent article) or hydrophilic. Suitable nucleating agents include, but are not limited to, boron nitride and talc. Suitable binders include, but are not limited to, natural rubber, synthetic rubber, and PCL. Suitable fillers include, but are not limited to, $TiO_2$, carbon black and calcium carbonate. Hydrophobic agents include any of those recognized in the absorbent articles field, such as silicone and lower alkyl silicone halides.

Those skilled in the art will recognize that various means for introducing the liquid resin mixture can be employed. For example, the resin(s) can be introduced through an orifice by way of gravity, or as the result of a pressurized system. It will also be recognized that conditions under which the introduction of the liquid resin mixture takes place will affect the characteristics (e.g., fibril length, fibril diameter, fibril stiffness) of the fibrils prepared. Such conditions include, for example, the viscosity of the resin mixture itself, the solvent system employed (where relevant), and the diameter of the orifice through which the liquefied mixture is introduced. The liquid resin mixture is preferably introduced as a continuous stream through an orifice having a diameter of from about 0.1 mm to about 5 mm. More preferred is where the orifice has a diameter about 0.5 to about 2.0 mm. While the rate of delivery of the liquid resin mixture is not critical, a rate of from about 10 g/hour to about 1000 g/hour is preferred. Where desired, a plurality of orifices, each as described herein, may be used for introducing the liquid resin mixture.

With respect to the flow of gas in step b), any suitable gas may be employed. The temperature of the gas is preferably less than 150° C. The temperature is more preferably less than 120° C. Still more preferred is where the temperature is from about 20° C. to about 90° C. Most preferred is where the gas is at approximately ambient temperature. Examples of gases that can be used in the present processes include $N_2$, compressed air and steam. Preferred is air. Furthermore, any recognized means for creating the flow of gas can be used for introducing the gaseous substance.

The conditions under which the flow of gas is introduced will affect the characteristics of the resulting biodegradable fibrils of the present invention. For example, where a nozzle is used for introducing the gas, the orifice size and gas pressure will affect the characteristics of the fibrils. Those skilled in the art recognize that such conditions will vary depending on, for example, the resins used, the method of liquefication used in step a) of the process, and the angle at which the flow of gas is introduced relative to the flow of the liquefied resin mixture. Preferred processes are those where a nozzle having a diameter of from about 1 mm to about 10 mm is used. More preferred is where the nozzle has a diameter of from about 2 mm to about 6 mm. Most preferred is where the nozzle has a diameter of from about 4 mm to about 5 mm. Preferred processes are those where the flow of the gaseous substance is introduced at a pressure of from about 10 to about 200 pounds per square inch (psi). More preferred is where the pressure is from about 25 to about 100 psi. Most preferred is where the pressure is from about 30 to about 60 psi.

The angle between the flow of the liquid resin mixture and the flow of the gaseous substance may be between about 0° and about 170°. For purposes of illustration, where the liquid resin mixture and the gaseous substance are flowing in the same direction and parallel to one another, the angle between them is 0°. Accordingly, the only limitation is that the angle between the liquid flow and the gaseous flow cannot be 180°. Preferably, the angle is from about 0° to about 90°. Those skilled in the art will recognize that the device used for collecting (e.g., wire screen) the formed fibrils can be placed at various distances from the point where the flow of gas contacts the liquefied resin mixture. The distance utilized will depend on, among other things, the resin(s) employed and the fibril dimensions desired.

Where desired, a plurality of means for introducing the gaseous substance, each as described herein, may be used.

The fibrils made according to the processes of the present invention are useful in making, for example, biodegradable nonwoven substrates, which can be used in absorbent articles such as diapers and the like.

In another embodiment of the present invention, the fibrils and nonwoven fabrics described herein are useful in a variety of textile applications. Such applications include, for example, clothing, linens, towels, curtains, and carpets.

Biodegradable Fibrils

The fibrils of the present invention, which comprise any biodegradable polymeric resin or resins, are made according to the processes of the present invention. Examples of resins useful in the present invention are discussed in detail above. The fibrils preferably comprise PHB or PHBV.

The fibrils of the present invention are preferably from about 0.5 mm to about 100 mm in length. More preferred are from about 1 mm to about 50 mm in length. Most preferred are fibrils having a length of from about 2 mm to about 10 mm. The fibrils of the present invention are preferably from about 1 µm to about 500 µm in diameter. More preferred are fibrils having a diameter of from about 1 µm to about 200 µm. Still more preferred are fibrils from about 5 µm to about 50 µm in diameter.

The preferred ranges listed refer to the fibrils of the invention generally. Preferred fibril dimensions will depend upon the polymeric resins utilized, the specific process employed and, the desired end-use of the resulting fibrils.

Nonwoven Fabrics

The nonwoven fabrics of the present invention comprise fibrils comprising one or more biodegradable polymers or copolymers. The preferred means for preparing the nonwoven fabrics of the present invention are the processes of the present invention. In general, the processes of the present invention will form fibrils that are already in the form of a nonwoven fabric. As such, minimal additional processing may be necessary, depending on the end-use of the nonwoven fabric.

Nonetheless, the biodegradable nonwoven fabrics may also be prepared according to methods for preparing conventional nonwoven fabrics, so long as the processes do not use conditions (e.g., temperatures) that will cause decomposition of the biodegradable resins used. See ENCYCLOPEDIA OF POLYMER SCIENCE AND ENGINEERING, Second Edition, Vol. 7, pp 647–733 (1983). For example, fibrils may be prepared by cutting essentially continuous fibers to desired fibril length. Additional steps can then be performed to prepare the desired nonwoven fabric.

The fibrils of the present invention are generally shorter than conventional fibers used in fabric-making. Accordingly, if additional processing of the fibrils to give a nonwoven fabric is desired, preferred is the use of modified paper making techniques. For example, after initial formation, the biodegradable fibrils may be continuously dispersed in a large volume of a nonsolvent (e.g. water) and collected on a moving endless wire screen. Once the nonwoven fabric is collected on the screen, it is transferred to belts or felts and dried on heated drums (see ENCYCLOPEDIA OF POLYMER SCIENCE AND ENGINEERING, Second Edition, Vol. 10, pp 204–226).

Importantly, a nonwoven fabric of the present invention may comprise biodegradable fibrils made from different resin mixtures. That is, two or more types of fibril, each made using the processes of the present invention, may be combined to form a single nonwoven fabric. While the distinct fibrils will be prepared using the processes of the present invention, the fibrils will subsequently be combined using, for example, the modified paper making techniques described herein.

Furthermore, during the formation of nonwoven fabrics, it is possible to combine with the biodegradable fibrils of the present invention one or more of a variety of natural fibers, such as polysaccharides and polyamides. Thus, the fibrils of the present invention can be combined with cellulose-based fibers, such as wood pulp and cotton, or protein-based fibers such as silk and wool. These naturally occurring fibers can be combined with the fibrils of the present invention using, for example, the paper-making techniques discussed above.

The bonding of fibrils and other components gives strength to the fabric and influences other properties of the nonwoven fabric. Both adhesive and mechanical means are used for bonding within the fabric. Mechanical bonding employs the engagement of fibrils by frictional forces. Bonding can also be achieved by chemical reaction, i.e., formation of covalent bonds between binder and fibrils.

Absorbent Articles

The disposable absorbent articles of the present invention comprise a water-permeable topsheet, an absorbent core, and a water-impermeable backsheet, wherein the topsheet comprises a nonwoven substrate comprising biodegradable fibrils.

Biodegradable substrates comprising fibrils of the present invention used as liquid pervious topsheets in absorbent articles of the present invention, such as disposable diapers, typically have a thickness of from about 25 µm to about 1 mm, preferably from about 100 µm to about 500 µm.

In general, the liquid pervious topsheet is combined with a liquid impervious backsheet and an absorbent core positioned between the topsheet and the backsheet. Optionally, elastic members and tape tab fasteners can be included. While the topsheet, the backsheet, the absorbent core and elastic members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975. The backsheet can be prepared from either biodegradable or nonbiodegradable materials. Examples of nonbiodegradable backsheets are those made from polypropylene and polyethylene.

Examples of biodegradable backsheets are those described in co-pending applications U.S. patent application Ser. No. 08/187,969, titled BIODEGRADABLE COPOLYMERS AND PLASTIC ARTICLES COMPRISING BIODEGRADABLE COPOLYMERS; U.S. Ser. No. 08/188,271; and U.S. Ser. No. 08/189,029; all filed by Noda on Jan. 28, 1994. To enhance compostability, preferred absorbent articles of the present invention comprise a biodegradable backsheet.

The topsheet is preferably soft-feeling, and non-irritating to the wearer's skin, while at the same time being compostable. Accordingly, the topsheet preferably comprises the biodegradable fibers of the present invention. Further, the topsheet is liquid pervious, permitting liquids to readily penetrate through its thickness. Preferably, the topsheet is treated with a hydrophobic material to isolate the wearer's skin from liquids in the absorbent core.

Preferably, the topsheet has a real density of from about 18 to about 25 $g/m^2$, a minimum dried tensile strength of at least about 400 g/cm in the machine direction, and a wet tensile strength of at least about 55 g/cm in the cross-machine direction.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means such as an adhesive or any other attachment means known in the art. For example, a uniform, continuous layer of adhesive, a patterned layer of adhesive, or an array of separate lines or spots of adhesive may be used to affix the topsheet to the backsheet.

Tape tab fasteners are typically applied to the back waistband region of the diaper to provide a fastening means for holding the diaper on the wearer. The tape tab fasteners can be any of those well known in the art, such as the fastening tape disclosed in U.S. Pat. No. 3,848,594 issued to Kenneth B. Buell on Nov. 19, 1974. These tape tab fasteners or other diaper fastening means are typically applied near the corners of the diaper.

Preferred diapers have elastic members disposed adjacent the periphery of the diaper, preferably along each longitudinal edge so that the elastic members tend to draw and hold the diaper against the legs of the wearer. The elastic members are secured to the diaper in a contractible condition so that in a normally unrestrained configuration the elastic members effectively contract or gather the diaper. The elastic members can be secured in an contractible condition in at least two ways. For example, the elastic members may be stretched and secured while the diaper is in an uncontracted condition. Alternatively, the diaper may be contracted, for example, by pleating, an elastic member secured and connected to the diaper while the elastic members are in their relaxed or unstretched condition.

The elastic members may take a multitude of configurations. For example, the width of the elastic members may be varied from about 0.25 mm to about 25 mm or more; the elastic members may comprise a single strand of elastic material or the elastic members may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, or the elastic members may simply be glued to the diaper.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article or diaper. Further, the size and absorbent capacity of the absorbent core may vary to accommodate wearers ranging from infants through adults.

A preferred embodiment of the diaper has an hour-glass shaped absorbent core. The absorbent core is preferably an absorbent member comprising a web or batt of airfelt, wood pulp fibers, and/or a particulate absorbent polymeric composition disposed therein.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees J. Van Tilburg on Aug. 18, 1987, and in U.S. Pat. No. 4,589,876, entitled "Sanitary Napkin" which issued to Kees J. Van Tilburg on May 20, 1986. It will be apparent that the fibrils of the present invention described herein may be used as the liquid pervious topsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The topsheet comprises fibrils of the present invention. The backsheet may comprise any of the backsheet materials discussed with respect to diapers. Preferred are topsheets comprising biodegradable fibrils made by the processes of the present invention. The absorbent core may comprise any of the absorbent core materials discussed with respect to diapers.

Importantly, the absorbent articles according to the present invention are biodegradable and/or compostable to a greater extent than conventional absorbent articles which employ materials such as a polyolefin (e.g., a polyethylene) topsheet.

Textiles

The textiles of the present invention may be prepared directly from the nonwoven fabrics of the present invention. Thus, the textiles will comprise as a primary material only the biodegradable nonwoven fabric of the present invention.

Alternatively, the textiles of the present invention can be prepared by combining biodegradable fibrils of the present invention with other fibers, preferably biodegradable fibers such as cotton, rayon, hemp, wool, and silk, to form fabrics, threads or yarns. The textiles can be prepared by using known methods for making textile articles. Such methods are described in KIRK-OTHMER ENCYCLOPEDIA OF CHEMICAL TECHNOLOGY, 3rd edition, Vol. 22, pp 762–768 (1986), which is incorporated by reference herein.

Regardless of the method of preparation, the textiles of the present invention are far ranging in their application areas. Such applications include, for example, apparel, bedding sheets, upholstery, carpeting, wall covering, tire reinforcement, tenting, filter media, conveyor belts and insulation. The textiles of the present invention are biodegradable and/or compostable to a greater extent than conventional textiles known in the art.

EXAMPLE 1

Process for Making a Nonwoven Fabric Comprising Poly(3-hydroxybutyrate-co-3-hydroxyvalerate)

Poly(3-hydroxybutyrate-co-3-hydroxyvalerate) resin with the comonomer content of 12-mol % hydroxyvalerate (BIOPOL, ICI, Billingham UK) is extruded by using a twin-srew extruder (HMKE SYSTEM 90, -Haake, Paramus N.J.) equipped with a Capillary Die with, 0.5 mm diameter. The resin is supplied to the extruder in pellet form. The extruder speed is set to 5.0 rpm and the extrusion temperature is set to 180° C. The extrudate coming out of the exiting port of the extruder die is allowed to flow down vertically in air without any support for about 50 cm to attain steady thin continuous strand of molten resin before being subjected to a sudden downward jet flow of air. The air jet is supplied by connecting an air flow nozzle (TRANSVECTOR JET #901D, Vortec Corp., Cincinnati Ohio) attached to a compressed air source with 80-psi pressure. The air jet applied parallel to the downward free flow of molten resin produces a rapid steady downward stream of fine highly elongated fibrils having a diameter between 10 to 100 µm and a length from about 5 to 50 mm. The fibrils are collected to form a continuous nonwoven fabric over a mesh screen located about 30 cm away from the point where the air jet is applied.

EXAMPLE2

Process for Making a Nonwoven Comprising Poly (ε-caprolactone)

Poly(ε-caprolactone) resin (TONE P787, Union Carbide, Danbury Conn.) is extruded by using a twin-screw extruder (HAAKE SYSTEM 90, Haake, Paramus N.J.) equipped with a Capillary Die with 0.5 mm diameter. The resin is supplied to the extruder in pellet form. The extruder speed is set to 3.0 rpm and the extrusion temperature is set to 240° C. The extrudate coming out of the exiting port of the extruder die is allowed to flow down vertically in air without any support for about 50 cm to attain steady thin continuous strand of molten resin before being subjected to a sudden jet flow of air. The air jet is supplied by connecting a nozzle with a diameter of 3.2 mm attached to a compressed air source with 80-psi pressure. The air jet applied to the downward free flow of molten resin produces a rapid steady horizontal stream of fine highly elongated fibrils having a diameter of from about 10 to 100 µm and a length from about 5 to 50 mm. The fibrils are collected to form a continuous nonwoven fabric over a mesh screen located about 2 m away from the point where the air jet is applied.

EXAMPLE 3

Process for Making a Nonwoven Fabric Comprising Poly(3-hydroxybutyrate)

Poly(3-hydroxybutyrate) resin (BIOPOL, ICI, Billingham UK) is extruded by using a twin-screw extruder (HAAKE SYSTEM 90, Haake, Paramus N.J.) equipped with a Capillary Die with 1.0 mm diameter. The resin is supplied to the extruder in pellet form. The extruder speed is set to 3.0 rpm and the extrusion temperature is set to 180° C. The extrudate coming out of the exiting port of the extruder die is allowed to flow down vertically in air without any support for about 50 cm to attain steady thin continuous strand of molten resin before being subjected to a sudden downward jet flow of air. The air jet is supplied by connecting an air flow nozzle (TRANSVECTOR JET #901D, Vortec Corp., Cincinnati Ohio) attached to a compressed air source with 100 psi pressure. The air jet applied parallel to the downward free flow of molten resin produces a rapid steady downward stream of fine highly elongated fibrils having a diameter from about 10 to 100 µm and a length from about 5 to 50 mm. The fibrils are collected to form a continuous nonwoven fabric over a mesh screen located about 30 cm away from the point where the air jet is applied.

EXAMPLE 4

Process for Making a Nonwoven Fabric Comprising Poly(3-hydroxybutyrate-co-3-hydroxyvalerate)

A 10%-solution of poly(3-hydroxybutyrate-co-3-hydroxyvalerate) resin with the comonomer content of 12-mol % hydroxyvalerate (BIOPOL, ICI, Billingham UK) in chloroform (J. T. Baker, Phillipsberg N.J.) is produced by dissolving 40 g of resin in 360 g of solvent with stirring and moderate heating. The solution is poured down through a 5-mL glass pipette with a 3-mm diameter tip to flow vertically in air without any support for about 5 cm to attain steady thin continuous strand of the solution before being subjected to a sudden downward jet flow of air.

The air jet is supplied by connecting an air flow nozzle (TRANSVECTOR JET #901D, Vortec Corp., Cincinnati Ohio) attached to a compressed air source with 90-psi pressure. The air jet applied parallel to the downward free flow of the solution instantaneously evaporates the solvent and produces a rapid steady downward stream of fine highly elongated fibrils having a diameter of about 10 µm and a length of from about 3 to 25 mm. The fibrils are collected to form a continuous nonwoven fabric over a mesh screen located about 70 cm away from the point where the air jet is applied.

EXAMPLE 5

Process for Making a Nonwoven Fabric Comprising Poly(3-hydroxybutyrate-co-3-hydroxyvalerate) and Poly(ε-caprolactone)

A 5%-solution of a 19:1 resin mixture of poly(3-hydroxybutyrate-co-3-hydroxyvalerate) with the comonomer content of 12-mol % hydroxyvalerate (BIOPOL, ICI, Billingham UK) and poly(ε-caprolactone) (TONE P787, Union Carbide, Danbury Conn.) in chloroform (J. T. Baker, Phillipsberg N.J.) is produced by dissolving a mixture of 30 g of poly(3-hydroxybutyrate-co-3-hydroxyvalerate) and 2 g of poly(ε-caprolactone) in 760 g of solvent with stirring and moderate heating. The solution is poured down through a 5-mL glass pipette with a 3-mm diameter tip to flow vertically in air without any support for about 5 cm to attain steady thin continuous strand of the solution before being subjected to a sudden downward jet flow of nitrogen. The nitrogen jet is supplied by connecting an air flow nozzle (TRANSVECTOR JET #901D, Vortec Corp., Cincinnati Ohio) attached to a compressed nitrogen source with 80-psi pressure. The nitrogen jet applied parallel to the downward free flow of the solution instantaneously evaporates the solvent and produces a rapid steady downward stream of fine highly elongated fibrils having a diameter of about 10 µm and a length from about 3 to 25 mm. The fibrils are collected to form a continuous nonwoven fabric over a mesh screen located about 70 cm away from the point where the nitrogen jet is applied. The resulting nonwoven fabric is heat cured in an oven at 120° C. for 2 hours.

EXAMPLE 6

Process for Making a Nonwoven Fabric Comprising Poly(3-hydroxybutyrate-co-3-hydroxyvalerate) and Poly(lactic acid)

A 5%-solution of a 9:1 resin mixture of poly(3-hydroxybutyrate-co-3-hydroxyvalerate) with the comonomer content of 5-mol % hydroxyvalerate (BIOPOL, ICI, Billingham UK) and poly(lactic acid) (Polyscience, Inc.) in chloroform (J. T. Baker, Phillipsberg N.J.) is produced by dissolving a mixture of 9 g of poly(3-hydroxybutyrate-co-3-hydroxyvalerate) and 1 g of poly(lactic acid) in 190 g of solvent with stirring and moderate heating. The solution is poured down through a 5-mL glass pipette with a 3-mm diameter tip to flow vertically in air without any support for about 5 cm to attain steady thin continuous strand of the solution before being subjected to a sudden downward jet flow of nitrogen. The nitrogen jet is supplied by connecting an air flow nozzle (TRANSVECTOR JET #901D, Vortec Corp., Cincinnati Ohio) attached to a compressed nitrogen source with 80-psi pressure. The nitrogen jet applied parallel to the downward free flow of the solution instantaneously evaporates the solvent and produces a rapid steady downward stream of fine highly elongated fibrils having a diameter between 3 to 7 µm and a length from about 3 to 25 mm. The fibrils are collected to form a continuous nonwoven fabric over a mesh screen located about 70 cm away from the point where the nitrogen jet is applied. The resulting nonwoven fabric is heat cured in an oven at 120° C. for 1 hour.

EXAMPLE 7

Process for Making a Nonwoven Fabric Comprising Poly(3-hydroxybutyrate)

A 10%-solution of a poly(3-hydroxybutyrate) resin (BIOPOL, ICI, Billingham UK) in chloroform (J. T. Baker, Phillipsberg N.J.) is produced by dissolving 10 g of poly(3-hydroxybutyrate) in 90 g of solvent with stirring and moderate heating. The solution is poured down through a 5-mL glass pipette with a 3-mm diameter tip to flow vertically in air without any support for about 5 cm to attain steady thin continuous strand of the solution before being subjected to a sudden downward jet flow of nitrogen. The nitrogen jet is supplied by connecting a nozzle with a diameter of 3.2 mm attached to a compressed air source with 80-psi pressure. The nitrogen jet applied to the downward free flow of molten resin instantaneously evaporates the solvent and produces a rapid steady horizontal stream of fine highly elongated fibrils having a diameter about 10 µm and a length from about 3 to 25 mm. The fibrils are collected to form a continuous nonwoven fabric over a mesh screen located about 2 m away from the point where the nitrogen jet is applied. The resulting nonwoven fabric is heat cured in an oven at 120° C. for 1 hour.

EXAMPLE 8

Compostable Disposable Diaper

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.020–0.038 mm film consisting of polyethylene (as described in U.S. Pat. No. 3,860,003, issued Jan. 14, 1974 to Buell, which is incorporated herein by reference); width at top and bottom 33 cm; notched inwardly on both sides to a width-at-center of 28.5 cm; length 50.2 cm.

2. Topsheet: comprises the nonwoven fabric prepared in Example 1; width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE 9

Compostable Lightweight Pantiliner

A lightweight pantiliner suitable for use between menstrual periods comprises a pad (surface area 117 cm$^2$; SSK air felt 3.0 g) containing 1.0 g of absorbent gelling material particles (commercial polyacrylate; Nippon Shokubai); said pad being interposed between a topsheet according to Example 1 and a backsheet which comprises a 0.03 mm thickness polyethylene film.

EXAMPLE 10

Compostable Sanitary Napkin

A catamenial product in the form of a sanitary napkin having two flaps extending outward from its absorbent core is prepared using a pad in the manner of Example 9 (surface area 117 cm$^2$; 8.5 g SSK air felt), per the design of U.S. Pat. No. 4,687,478, Van Tilburg, Aug. 18, 1987. The backsheet and topsheet materials are the same as described in Example 9.

EXAMPLE 11

Heat-cured Compostable Nonwoven Fabric

The fabric of Example 1 is collected on a cardboard mat. The mat is moved in a fashion so that a 10 cm×10 cm area is covered uniformly with fibrils. Collection of fibrils on the mat continues, until there is approximately 0.5 cm thick fibril mat. A wide distribution of fibril lengths are obtained, up to 100 mm in length. Most fibril lengths (over 50%) are in the range of 5 to 20 mm. The mat is then transferred to a Carver Press (Fred S. Carver Inc., Menomonee Falls, Wis.) and pressed at a 1000 lb force for 10 minutes at temperature 5° C. below the melting temperature of the PHBV. The resulting nonwoven sheet is removed from the press.

EXAMPLE 12

Compostable Disposable Diaper

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.020–0.038 mm film consisting of a 92:8 poly(3-hydroxybutyrate-co-3-hydroxyoctanoate) copolymer (prepared as described in U.S. patent application Ser. No. 08/187,969, titled BIODEGRADABLE COPOLYMERS AND PLASTIC ARTICLES COMPRISING BIODEGRADABLE COPOLYMERS, by Noda, filed Jan. 28, 1994); width at top and bottom 33 cm; notched inwardly on both sides to a width-at-center of 28.5 cm; length 50.2 cm.

2. Topsheet: comprises the nonwoven fabric prepared in Example 1; width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE 13

Compostable Lightweight Pantiliner

A lightweight pantiliner suitable for use between menstrual periods comprises a pad (surface area 117 cm$^2$; SSK air felt 3.0 g) containing 1.0 g of absorbent gelling material particles (commercial polyacrylate; Nippon Shokubai): said pad being interposed between a topsheet according to Example 1 and a backsheet which comprises a 0.03 mm thickness 92:8 poly(3-hydroxybutyrate-co-hydroxyoctanoate) copolymer film (as described in U.S. patent application Ser. No. 08/187,969 titled BIODEGRADABLE COPOLYMERS AND PLASTIC ARTICLES COMPRISING BIODEGRADABLE COPOLYMERS, by Noda, filed Jan. 28, 1994).

EXAMPLE 14

Compostable Sanitary Napkin

A catamenial product in the form of a sanitary napkin having two flaps extending outward from its absorbent core is prepared using a pad in the manner of Example 13 (surface area 117 cm$^2$; 8.5 g SSK air felt), per the design of U.S. Pat. No. 4,687,478, Van Tilburg, Aug. 18, 1987. The backsheet and topsheet materials are the same as described in Example 13.

EXAMPLE 15

Compostable Surgical Scrup

Apparel suitable for wearing by surgical staff which can be subsequently disposed of for biodegradation; said apparel comprising the nonwoven fabric of Example 7 sewn in the design of a pullover shirt and the nonwoven fabric of Example 7 sewn in the design of a pair of pants comprising a waist drawstring.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in spirit and purview of this application and scope of the appended claims.

What is claimed is:

1. Biodegradable fibrils made by a process for preparing biodegradable fibrils from one or more biodegradable homopolymeric or copolymeric resins, said process comprising:

a) forming a liquid resin mixture by melting or solvating the resin or resins; and b) introducing the liquid resin mixture to a flow of a gaseous substance.

2. The biodegradable fibrils of claim 1 wherein the fibrils are from about 2 mm to about 10 mm in length and from about 5 µm to about 500 µm in diameter.

3. The biodegradable fibrils of claim 1 wherein the fibrils comprise a biologically produced aliphatic polyester; a synthetic aliphatic polyester; polyvinyl alcohol or a copolymer thereof; a polyether; cellulose or a derivative thereof; or a mixture thereof.

4. The biodegradable fibrils of claim 3 wherein the fibrils comprise poly(hydroxybutyrate) or poly(hydroxybutyrate-co-hydroxyvalerate).

5. A nonwoven fabric comprising the biodegradable fibrils of claim 1.

6. The nonwoven fabric of claim 5 wherein the fibrils are from about 2 mm to about 10 mm in length and from about 5 µm to about 500 µm in diameter.

7. The nonwoven fabric of claim 5 wherein the fibrils comprise a biologically produced aliphatic polyester; a synthetic aliphatic polyester; a polyvinyl alcohol or a copolymer thereof; a polyether; cellulose or a derivative thereof; or a mixture thereof.

8. The nonwoven fabric of claim 7 wherein the fibrils comprise poly(hydroxybutyrate) or poly(hydroxybutyrate-co-hydroxy-valerate).

9. A disposable absorbent article comprising a water-permeable topsheet, an absorbent core, and a water-impermeable backsheet, wherein the topsheet comprises a nonwoven substrate comprising the biodegradable fibrils of claim 1.

10. The disposable absorbent article of claim 9, wherein said biodegradable fibrils are from about 2 mm to about 10 mm in length and from about 5 µm to about 500 µm in diameter.

11. The disposable absorbent article of claim 9 wherein the biodegradable fibrils comprise a biologically produced aliphatic polyester; a synthetic aliphatic polyester; a polyvinyl alcohol or a copolymer thereof; a polyether; cellulose or a derivative thereof; or a mixture thereof.

12. The disposable absorbent article of claim 11 wherein the biodegradable fibrils comprise one biodegradable resin, and wherein said resin is poly(hydroxybutyrate) or poly (hydroxybutyrate-co-hydroxyvalerate).

13. A textile comprising the biodegradable fibrils of claim 1.

14. The fibrils of claim 1, wherein said process comprises:

a) forming a liquid resin mixture by melting or solvating the resin or resins; and b) introducing the liquid resin mixture to a flow of a gaseous substance; at about 5 cm to about 50 cm away from the bulk mixture.

15. The fibrils of claim 1, wherein said process comprises:

a) forming a liquid resin mixture by melting or solvating the resin or resins; and b) introducing the liquid resin mixture to a flow of a gaseous substance; at about 5 cm away from the bulk mixture.

16. The fibrils of claim 1, wherein said process comprises:

a) forming a liquid resin mixture by melting or solvating the resin or resins; and b) introducing the liquid resin mixture to a flow of a gaseous substance; at about 50 cm away from the bulk mixture.

* * * * *